United States Patent [19]

Umezawa et al.

[11] 4,147,861
[45] Apr. 3, 1979

[54] 1N-(α-HYDROXY-ω-AMINOALKANOYL)-6′N-METHYL-3′,4′-DIDEOXYKANAMYCIN B AND THE PRODUCTION THEREOF

[75] Inventors: Hamao Umezawa; Kenji Maeda, both of Tokyo; Shinichi Kondo, Yokohama; Sumio Umezawa, Tokyo, all of Japan

[73] Assignee: Zaidan Hojin Biseibutsu Kagaku Kenkyu Kai, Tokyo, Japan

[21] Appl. No.: 865,470

[22] Filed: Dec. 29, 1977

Related U.S. Application Data

[63] Continuation of Ser. No. 616,466, Sep. 24, 1975, abandoned.

[51] Int. Cl.$^2$ ............................................. C07H 15/22
[52] U.S. Cl. .................................... 536/10; 424/180; 536/17
[58] Field of Search .................................... 536/10, 17

[56] References Cited

U.S. PATENT DOCUMENTS

| 3,925,353 | 12/1975 | Umezawa et al. | 536/10 |
| 3,929,762 | 12/1975 | Umezawa et al. | 536/17 |
| 3,939,143 | 2/1976 | Umezawa et al. | 536/10 |

OTHER PUBLICATIONS

Kondo et al., "The Journal of Antibiotics", vol. XXVII, No. 1, 1974, pp. 90–93.

*Primary Examiner*—Johnnie R. Brown
*Attorney, Agent, or Firm*—Herbert W. Taylor, Jr.

[57] ABSTRACT

A number of 1N-(α-hydroxy-ω-aminoalkanoyl)-6′N-methyl-3′,4′-dideoxykanamycin B derivatives have been found to possess excellent antibacterial activity against most kanamycin susceptible and resistant organisms. In particular, 1N-(DL-isoseryl)-6′N-methyl-3′,4′-dideoxykanamycin B, 1N-(L-isoseryl)-6′-N-methyl-3′,4′-dideoxykanamycin B, 1N-(L-4-amino-2-hydroxybutyryl)-6′N-methyl-3′,4′-dideoxykanamycin B and 1N-(L-5-amino-2-hydroxyvaleryl)-6′N-methyl-3′,4′-dideoxykanamycin B, or an acid addition salt thereof possess these highly desirable attributes.

5 Claims, No Drawings

1N-(α-HYDROXY-ω-AMINOALKANOYL)-6′N-METHYL-3′,4′-DIDEOXYKANAMYCIN B AND THE PRODUCTION THEREOF

CROSS-REFERENCE TO PRIOR APPLICATION

This application is a continuation of our prior, co-pending application Ser. No. 616,466 filed Sept. 24, 1975 and now abandoned.

BACKGROUND OF THE INVENTION

1. Field of the Invention

This invention relates to the preparation of new semi-synthetic 1-substituted derivatives of 6′N-methyl-3′,4′-dideoxykanamycin B, said compounds being prepared by selectively acylating the 1-amino-function with a α-hydroxy-ω-aminoalkanoyl moiety.

2. Description of the Prior Art

A. Kanamycin B is a known antibiotic described in Merck Index, 8th Edition, pp. 597–598. Kanamycin B is a compound having the formula

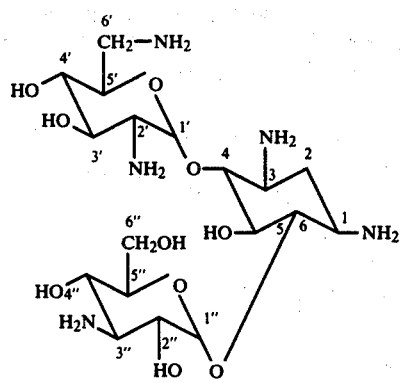

B. 6′N-Methyl-3′,4′-dideoxykanamycin B is a known compound described in British Pat. No. 1,384,221 and has the formula

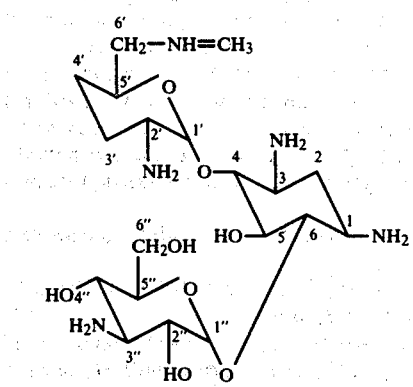

C. 3′,4′-Dideoxykanamycin B is described in U.S. Pat. No. 3,753,973 and has the formula

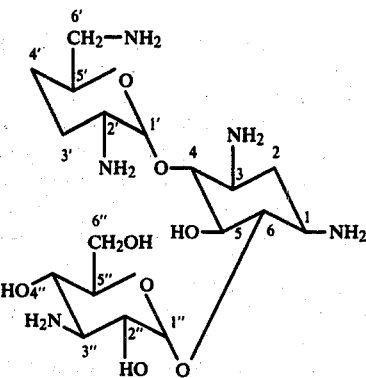

D. 1N-(L-4-Amino-2-hydroxybutyryl)kanamycin A and 1N-(L-4-amino-2-hydroxybutyryl)kanamycin B are described in U.S. Pat. No. 3,781,268 and have the formula

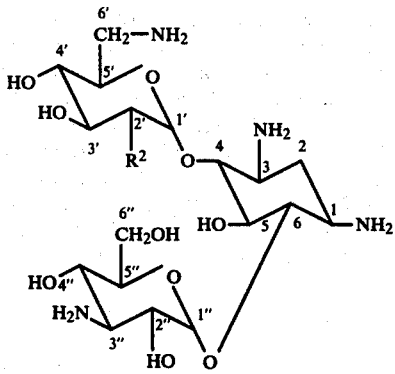

E. The compounds of the instant invention are described in The Journal of Antibiotics, 28, 340 (1975).

SUMMARY OF THE INVENTION

The compound having the formula

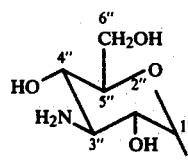
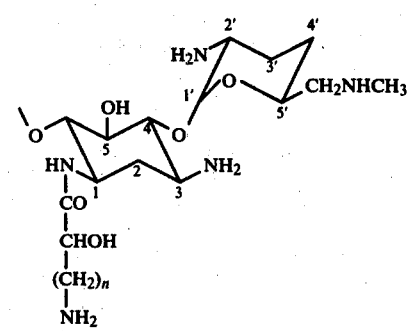

wherein n is 1, 2 or 3; or a pharmaceutically acceptable acid addition salt thereof are valuable antibacterial agents useful in the treatment of bacterial infections in animals.

COMPLETE DISCLOSURE

This invention relates to a new kanamycin B derivatives which are selected from the group consisting of 1N-(DL-isoseryl)-6'N-methyl-3',4'-dideoxykanamycin B, 1N-(L-isoseryl)-6'N-methyl-3',4'-dideoxykanamycin B, 1N-(L-4-amino-2-hydroxybutyryl)-6'N-methyl-3',4'-dideoxykanamycin B and 1N-(L-5-amino-2-hydroxyvaleryl)-6'N-methyl-3',4'-dideoxykanamycin B and/or a nontoxic, pharmaceutically acceptable acid addition salt thereof. Furthermore, this invention also relates to a process for the semi-synthetic production of these 1N-(α-hydroxy-ω-aminoalkanoyl)-6'N-methyl derivatives of 3',4'-dideoxykanamycin B.

Kanamycins A and B are known aminoglycosidic antibiotics and have been widely used as chemotherapeutic agents. However, many kanamycin-resistant strains of bacteria have developed in recent years. For instance, it has been found that some R-factor carrying strains of the gram-negative bacteria, such as *Escherichia coli* and *Pseudomonas aeruginosa*, have been isolated from patients which are resistant to the antibacterial action of the kanamycins. The mechanism of resistance of the kanamycin-resistant bacteria to the known aminoglycosidic antibiotics has been studied by H. Umezawa et al., Advances in Carbohydrate Chemistry and Biochemistry, Vol. 30, pp. 183–225, 1974, Academic Press. It has been discovered that some kanamycin-resistant bacteria produce enzymes capable of phosphorylating the 3'-hydroxyl group of the kanamycins and inactivate the kanamycins via these phosphotransferases and that some kanamycin-resistant bacteria produce an enzyme capable of nucleotidylating the 2"-hydroxyl group of the kanamycins and thereby inactivate the kanamycins via a nucleotidyltransferase, and that some other kanamycin-resistant bacteria produce enzymes capable of acetylating the 6'-amino group of the kanamycins and thereby inactivate the kanamycins via these acetyltransferases. In this way, the relationship of the molecular structure of the aminoglycosidic antibiotics to their antibacterial activity, as well as the biochemical mechanism of resistance of the kanamycin-resistant bacteria to the aminoglycosidic antibiotics have been elucidated.

Several semi-synthetic derivatives of the kanamycins which are active against the kanamycin-resistant bacteria have been synthetized from the parent kanamycins. Thus, 3',4'-dideoxykanamycin B (U.S. Pat. No. 3,753,973); 6'N-methyl-3',4'-dideoxykanamycin B (British Pat. No. 1,384,221); 1N-(L-4-amino-2-hydroxybutyryl)-kanamycin A and -kanamycin B (U.S. Pat. No. 3,781,268); and a 1N-(α-hydroxy-ω-aminoalkanoyl)-3',4'-dideoxykanamycin B (DT-OS No. 2,350,169) are synthesized, for example. These semi-synthetic kanamycin derivatives have been found to be active against a large number of kanamycin-resistant bacteria.

We have now performed further research in an attempt to provide new and useful derivatives of 3',4'-dideoxykanamycin B which are effective not only against the gram-negative and gram-positive bacteria sensitive to the kanamycins but also against the kanamycin-resistant bacteria. We have now found that selective acylation of the 1-amino group of 6'N-methyl-3',4'-dideoxykanamycin B with an α-hydroxy-ω-amino acid selected from the group consisting of isoserine, 4-amino-2-hydroxybutyric acid or 5-amino-2-hydroxyvaleric acid, either in racemic form or in the form of the L-isomer or in the form of the D-isomer, produces new and useful kanamycin B derivatives which exhibit high antibacterial activity against the gram-negative and gram-positive bacteria sensitive to the kanamycins, as well as against the bacteria resistant to the kanamycins.

An object of this invention was to provide new and useful kanamycin B derivatives which exhibit useful antibacterial activity against the kanamycin-resistant bacteria as well as against substantially all of the kanamycin-resistant bacteria producing the above-mentioned inactivating enzymes. Another object of this invention was to provide a process for the production of these new kanamycin B derivatives from 6'N-methyl-3',4'-dideoxykanamycin B, which is operable in a facile way and in a favorable yield of the desired product.

A preferred embodiment of the instant invention is the compounds having the formula

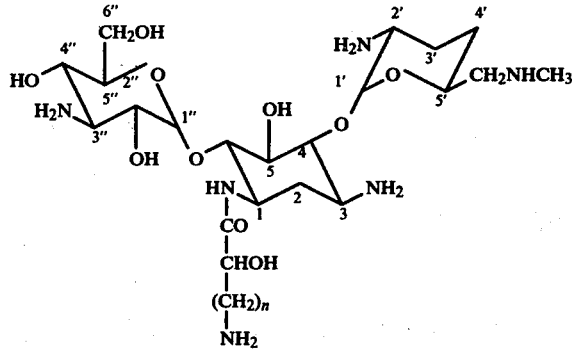

wherein n is 1, 2 or 3; and a pharmaceutically acceptable acid addition salt thereof. The α-hydroxy-ω-aminoalkanoyl moiety, that is, the isoseryl group, 4-amino-2-hydroxybutyryl group or 5-amino-2-hydroxyvaleryl group present in the molecule of the new compound of the above formula (I) may be either in the DL-form (namely, the racemic form), the L-form or the D-form.

The most preferred embodiments are the compounds:
(1) 1N-(DL-isoseryl)-6'N-methyl-3',4'-dideoxykanamycin B;
(2) 1N-(L-isoseryl)-6'N-methyl-3',4'-dideoxykanamycin B;
(3) 1N-(L-4-amino-2-hydroxybutyryl)-6'N-methyl-3',4'-dideoxykanamycin B; and
(4) 1N-(L-5-amino-2-hydroxyvaleryl)-6'N-methyl-3',4'-dideoxykanamycin B; or a pharmaceutically acceptable, nontoxic acid addition salt thereof.

Examples of the pharmaceutically acceptable acid addition salts of the new compounds of formula (I), according to this invention, include the hydrochloride, hydrobromide, sulfate, phosphate, nitrate, carbonate, acetate, maleate, fumarate, succinate, tartarate, oxalate, citrate, methanesulfonate, ethanesulfonate, ascorbate salts and the like, which may be a mono-, di-, tri-, tetra- or penta-salt formed by the interaction of one molecule of the new compound of the formula (I) with 1–5 moles of a nontoxic, pharmaceutically acceptable acid. The pharmaceutically acceptable acid includes hydrochloric, hydrobromic, sulfuric, phosphoric, nitric, carbonic, acetic, maleic, fumaric, succinic, tartaric, oxalic, methanesulfonic, ethanesulfonic, ascorbic acid and the like.

The new compounds according to this invention have the following physical, chemical and biological properties:

1N-(DL-isoseryl)-6′N-methyl-3′,4′-dideoxykanamycin B is a substance in the form of a colorless crystalline powder with a decomposition point of 165°–169° C., $[d]_D^{24} = +96°$ (c 1,175, water). Its elemental analysis is consistent with the theoretical values $C_{22}H_{44}N_6O_{10}$ (C, 47.81%, H, 8.03%, N, 15.21%). This substance gives a single spot (positive to the ninhydrin reaction) at Rf 0.51 by thin layer chlormatography on silica gel (available under a trade name "ART 5721", a product of Merck Co., Germany) when developed with n-butanol-ethanol-chloroform-28% aqueous ammonia (4:5:2:8 by volume).

1N-(L-isoseryl)-6′N-methyl-3′,4′-dideoxykanamycin B is a substance in the form of a colorless crystalline powder with a decomposition point of 162°–166° C., $[\alpha]_D^{24} = +80°$ (c, 1.02, water). Its elemental analysis is consistent with the theoretical values of $C_{22}H_{44}N_6O_{10}$ (C, 47.81%, H, 8.03%, N, 15.21%). This substance gives a single spot (positive to the ninhydrin reaction) at Rf 0.51 by the above-mentioned silica gel thin layer chromatography.

1N-(L-4-amino-2-hydroxybutyryl)-6′N-methyl-3′,4′-dideoxykanamycin B is a substance in the form of a colorless crystalline powder with a decomposition point of 158°–161° C., $[\alpha]_D^{25} = +71°$ (c, 0.8, water). Its elemental analysis is consistent with the theoretical values of $C_{23}H_{46}N_6O_{10}$ (C, 48.75%, H, 8.18%, N, 14.83%). This substance gives a single spot (positive to the ninhydrin reaction) at Rf 0.38 by the above-mentioned thin layer chromatography on silica gel.

1N-(L-5-amino-2-hydroxyvaleryl)-6′N-methyl-3′,4′-dideoxykanamycin B is the substance in the form of a colorless crystalline powder with a decomposition point of 152°–155° C., $[\alpha]_D^{24} = +79°$ (c, 0.71, water). Its elemental analysis is consistent with the theoretical values of $C_{24}H_{48}N_6O_{10}$ (C, 49.64%, H, 8.33%, N, 14,47%). This substance gives a single spot (positive to the ninhydrin reaction) at Rf 0.39 by the above-mentioned silica gel thin layer chromatography.

The new compounds of formula (I), according to this invention, are characterized in that they are not susceptible to all of the enzymatic, inactivating reactions with the above-mentioned enzymes which inactivate the kanamycin A and kanamycin B. Thus, the new compounds of this invention are neither susceptible to inactivation by the 6′-acetyltransferase because the 6′-amino group of the new compound of this invention has been methylated, nor are they susceptible to inactivation by the 2″-nucleotidyltransferase and the 3′-phosphotransferase beause the 1-amino group of the new compound of this invention has been acylated with the α-hydroxy-ω-aminoacyl group, nor are they susceptible to inactivation by the other type of the 3′-phosphotransferase because the 3′- and 4′-hydroxyl groups which are present in kanamycin B have been removed in the new compounds of this invention. Accordingly, the new compounds of this invention are remarkably advantageous in that they exhibit high antibacterial activity not only against various kinds of gram-negative and gram-positive bacteria which are sensitive to the kanamycins, but also against the kanamycin-resistant strains of these bacteria, particularly the kanamycin-resistant strains of *Escherichia coli* and *Pseudomonas aeruginosa*.

The minimum inhibitory concentrations (mcg./ml.) of 1N-(DL-isoseryl)-6′N-methyl-3′,4′-dideoxykanamycin B (abbreviated as DL-IS-MDKB); 1N-(L-isoseryl)-6′N-methyl-3′,4′-dideoxykanamycin B (abbreviated as L-IS-MDKB); 1N-(L-4-amino-3-hydroxybutyryl)-6′N-methyl-3′,4′-dideoxykanamycin B (abbreviated as AHB-MDKB); and 1N-(L-5-amino-2-hydroxyvaleryl)-6′N-methyl-3′,4′-dideoxykanamycin B (abbreviated as AHV-MDBK) against various organisms were determined according to serial dilution method using nutrient agar medium at 37° C., the readings being made after 18 hours incubation. For the comparison purpose, the minimum inhibitory concentrations (mcg./ml.) of 1 N-(L-4-amino-2-hydroxybutyryl)-kanamycin A (abbreviated as AHB-KMA) and 1N-(L-4-2-hydroxybutyryl)-kanamycin B (abbreviated as AHB-KMB) which are known from U.S. Pat. No. 3,781,268 were also determined by the same manner as stated above.

The antibacterial spectra of the concerned compounds are shown in Table 1 below.

Table 1

| Test Organisms | Minimum Inhibitory Concentrations (mcg./ml.) | | | | |
|---|---|---|---|---|---|
| | DL-IS-MDKB | L-IS-MDKB | AHB-MDKB | AHV-MDKB | AHB-KMA |
| *Staphylococcus aureus* | <0.20 | <0.20 | <0.20 | <0.20 | <0.20 |
| *Staphylococcus aureus* FDA 209P | 0.78 | <0.20 | 0.78 | 0.39 | 0.39 |
| *Staphylococcus aureus* Terajima | <0.20 | <0.20 | <0.20 | <0.20 | <0.20 |
| *Sarcina lutea* PCI 1001 | 6.25 | 3.13 | 3.13 | 12.5 | 3.13 |
| *Bacillus anthracis* | <0.20 | <0.20 | <0.20 | <0.20 | <0.20 |
| *Bacillus subtilis* PCI 219 | <0.20 | <0.20 | <0.20 | <0.20 | <0.20 |
| *Bacillus subtilis* NRRL B-558 | <0.20 | <0.20 | <0.20 | <0.20 | <0.20 |
| *Bacillus cereus* ATCC 10702 | 3.13 | 1.56 | 3.13 | 1.56 | 0.78 |
| *Corynebacterium bovis* 1810 | 3.13 | 0.78 | 3.13 | 6.25 | 0.78 |
| *Mycobacterium smegmatis* ATCC 607 | 0.39 | 0.39 | 0.20 | 0.78 | <0.20 |
| *Shigella dysenteriae* JS 11910 | 6.25 | 3.13 | 3.13 | 3.13 | 3.13 |
| *Shigella flexneri* 4b JS 11811 | 3.13 | 1.56 | 3.13 | 3.13 | 3.13 |
| *Shigella sonnei* JS 11746 | 3.13 | 3.13 | 6.25 | 3.13 | 1.56 |
| *Salmonella typhosa* T-63 | 1.56 | 0.39 | 3.13 | 0.78 | 0.39 |
| *Salmonella enteritidis* 1891 | 3.13 | 0.78 | 1.56 | 0.78 | 0.78 |
| *Proteus vulgaris* OX 19 | 1.56 | 0.78 | 1.56 | 0.78 | 0.78 |
| *Klebsiella pneumoniae* PCT 602 | 1.56 | 0.78 | 0.78 | 0.78 | 0.39 |
| *Klebsiella pneumoniae* 22 No. 3038 | 3.13 | 1.56 | 3.13 | 3.13 | 1.56 |
| *Escherichia coli* NIHJ | 1.56 | 1.56 | 1.56 | 0.78 | 0.78 |

Table 1-continued

| Test Organisms | Minimum Inhibitory Concentrations (mcg./ml.) | | | | |
| --- | --- | --- | --- | --- | --- |
| | DL-IS-MDKB | L-IS-MDKB | AHB-MDKB | AHV-MDKB | AHB-KMA |
| *Escherichia coli* K-12 | 1.56 | 0.78 | 0.78 | 0.78 | 0.78 |
| *Escherichia coli* K-12 R5 | 3.13 | 1.56 | 1.56 | 1.56 | 0.39 |
| *Escherichia coli* K-12 ML 1629 | 1.56 | 1.56 | 1.56 | 0.78 | 0.78 |
| *Escherichia coli* K-12 ML 1630 | 3.13 | 1.56 | 0.78 | 1.56 | 0.78 |
| *Escherichia coli* K-12 ML 1410 | 3.13 | 1.56 | 1.56 | 1.56 | 0.78 |
| *Escherichia coli* K-12 ML 1410 R81 | 3.13 | 1.56 | 1.56 | 1.56 | 1.56 |
| *Escherichia coli* LA290 R55 | 3.13 | 1.56 | 0.78 | 0.78 | 0.78 |
| *Escherichia coli* LA290 R56 | 0.78 | 0.78 | 0.78 | 0.39 | 0.39 |
| *Escherichia coli* LA290 R64 | 0.78 | 0.39 | 0.78 | 0.39 | 0.39 |
| *Escherichia coli* W677 | 1.56 | 0.78 | 0.78 | 0.78 | <0.20 |
| *Escherichia coli* JR66/W677 | 3.13 | 1.56 | 3.13 | 1.56 | 1.56 |
| *Pseudomonas aeruginosa* A3 | 3.13 | 3.13 | 3.13 | 3.13 | 3.13 |
| *Pseudomonas aeruginosa* No. 12 | 6.25 | 25 | 3.13 | 25 | 3.13 |
| *Pseudomonas aeruginosa* TI-13 | 12.5 | 6.25 | 6.25 | 6.25 | 3.13 |
| *Pseudomonas aeruginosa* GN315 | 12.5 | 25 | 6.25 | 12.5 | 100 |
| *Pseudomonas aeruginosa* 99 | 25 | 25 | 25 | 25 | 6.25 |

The new compounds of this invention are of low toxicity to animals, including man, as they show LD$_{50}$ values of more than 100 mg./kg. upon intravenous injection of the compounds in mice. In addition, the new compounds of this invention exhibit high antibacterial activity against various gram-negative and gram-positive bacteria sensitive to kanamycins, as well as against the kanamycin-resistant strains thereof as stated hereinbefore, so that the new compounds of this invention may be useful in therapeutic treatment of infections by various gram-negative and gram-positive bacteria.

The compounds of this invention may be administered orally, intraperitoneally, intravenously, subcutaneously or intramuscularly using any pharmaceutical form known to the art for such administration and in a similar manner to kanamycins. For instance, the compounds of the formula (I) of this invention may be administered orally using any pharmaceutical form known to the art for such oral administration. Examples of pharmaceutical forms for oral administration are powders, capsules, tablets, syrup and the like. Suitable dose of the compound for the effective treatment of bacterial injections is in a range of 0.25-2 g. per person a day when it is given orally. It is preferred that said dose should be orally administered in three to four aliquots per day. The compounds of this invention may also be administered by intramuscular injection at a dosage of 50-500 mg. per dose two to four times per day. Moreover, the new compounds of the invention may be formulated into an ointment for external application which contains a compound of this invention at a concentration of 0.5-5% by weight in mixture with a known ointment base such as polyethylene glycol. Moreover, the compounds of this invention are useful to sterilize surgical instruments when the sterilization is accompanied by adequate mechanical cleansing.

In principle, the new compounds of the formula (I), according to this invention, may be prepared from a known compound, 6'N-methyl-3',4'-dideoxykanamycin B, of the formula

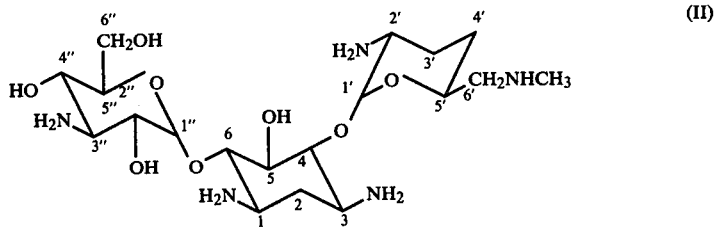

by selectively acylating the 1-amino group of 6'N-methyl-3',4'-dideoxykanamycin B with an α-hydroxy-ω-amino acid of the formula

wherein n is an integer of 1, 2 and 3, in a manner known per se in the prior art, consistent with the acylation of an amino group in the synthesis of peptides. The 6'N-methyl-3',4'-dideoxykanamycin B of formula II contains four free primary amino groups (1-, 3-, 2'- and 3''-amino groups) and one secondary methylamino group at the 6'-position. To produce the compounds of formula (I), according to this invention, it is required that the 1-amino group of 6'N-methyl-3',4'-dideoxykanamycin B be selectively acylated with the α-hydroxy-ω-amino acid of the formula (III) without causing the acylation of the other three amino groups and the 6'-methylamino group. The new compounds of the formula (I) are obtained in the best yield when the α-hydroxy-ω-amino acid reactant of the formula (III) is reacted with an amino-protected derivative of compound II in which the 6'-methylamino group and the free amino groups (that is, the 3-, 2'- and 3''-amino groups) other than the 1-amino group have been blocked by a known amino-protecting group with only the 1-amino group remaining free. The preparation of the amino-protected derivative is difficult but possible and a number of reaction steps are required for the preparation. It is preferred instead to prepare such an amino-protected derivative of compound II in which only the 6'methylamino group and optionally the 2'-amino group have been blocked by the amino-protecting group while the other amino groups are retained in the free state. Preparation of the latter type of the mono and di-amino-protected derivative of compound II is relatively easier to prepare due to the fact that the 6'-methylamino and the 2'-amino groups are more reactive than the other amino groups of compound II and hence can be blocked preferentially by the amino-protecting group while keeping the other amino groups unblocked. As the reactivity of the 2'-amino group is a little lower than that of the 6'-methylamino group but is higher than that of the 1-, 3- and 3"-amino groups, the 2'-amino group may also be blocked, if desired.

When the amino-protected derivative prepared from compound II in which the 6'-methylamino group and optionally the 2'-amino group have been blocked is reacted with the α-hydroxy-ω-amino acid (III) in which the ω-amino group may preferably be blocked by an amino-protecting group, there is formed a reaction product comprising mainly the desired 1N-mono-acylated derivative together with lesser quantities of the mono- and poly-N-acylated derivatives in which one or more of the amino groups other than the 1-amino group and occasionally the 2'-amino group have been acylated with the α-hydroxy-ω-amino acid (III), respectively. Thus, the acylation product resulting from the above reaction is actually obtained in the form of a mixture of differently N-acylated derivatives including the desired 1-N-mono-acylated derivative. It is possible to isolate the desired 1N-mono-acylated derivative from the mixed N-acylated derivatives by subjecting the mixture to a chromatographic separation. However, the mixed N-acylated derivatives may be directly treated to remove the amino-protecting groups therefrom. This produces a mixture of the desired 1N-mono-acylated product of the formula (I) with the otherwise mono- and poly-N-acylated, undesired by-products derived from the selectively amino-protected starting compound. The desired product (I) may be isolated from the undesired by-products by subjecting the mixture of them to a chromatographic separation.

According to the second object of this invention, there is provided a process for the production of the 1N-(α-hydroxy-ω-aminoalkanoyl)-6'N-methyl-3',4'-dideoxykanamycin B compounds of the aforesaid formula (I), which comprises selectively acylating the 1-amino group of an amino-protected derivative of 6'N-methyl-3',4'-dideoxykanamycin B represented by the formula

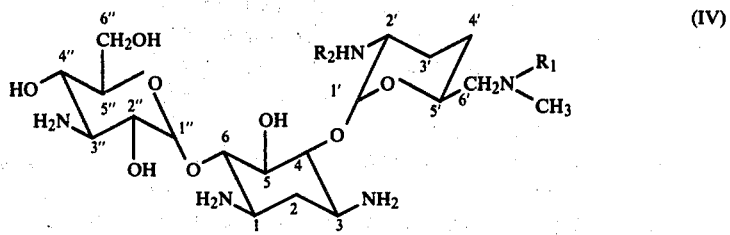

wherein $R_1$ is a known mono-valent amino-protecting group and $R_2$ is a hydrogen atom or a known mono-valent amino-protecting group, with an α-hydroxy-ω-amino acid of the formula

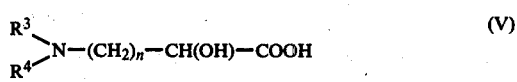

or its functional equivalent as an acylating agent, wherein $R_3$ is a known mono-valent amino-protecting group and $R_4$ is a hydrogen atom, or $R_3$ and $R_4$ taken together form a known di-valent amino-protecting group, and n is an integer of 1, 2 and 3, to produce a 1-N-acylated compound of the formula

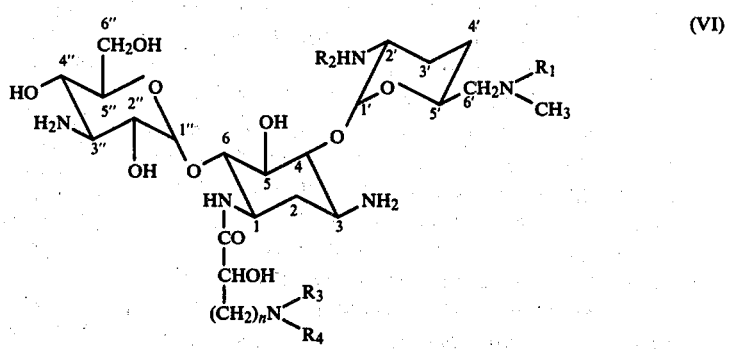

wherein $R_1$, $R_2$, $R_3$, $R_4$ and n are as defined above, and then removing the amino-protecting groups from said 1-N-acylated compound to produce the desired compound of the formula (I). This process may be followed by the additional step of isolating the desired compound of the formula (I) from any undesired N-acylated by-products.

To prepare the compound of the formula (IV) having the blocked 6'-methylamino group and the optionally blocked 2'-amino group which is employed as the starting material in the process of this invention, the compound of the formula (II) is treated with a reagent which is commonly used in the conventional synthesis of peptides for the purpose of introducing a known amino-protecting group into the amino acid employed. Accordingly, the amino-protecting group available in the process of this invention may be any of the known amino-protecting groups which are commonly used in the synthesis of peptides, as long as it is readily removable from the acylated derivative VI as produced in the acylation step of the present process. When the acylated derivative having the blocked amino groups is treated in a manner known for the removal of the amino-protecting group, the amino-protecting groups used must be removed readily without substantially affecting the amide linkage which has been formed between the α- hydroxy-ω-aminoalkanoyl radical and the 1-amino group in the said acylated derivative VI.

As suitable examples of the mono-valent amino-protecting groups for $R_1$, $R_2$, $R_3$ and $R_4$ in this invention, there may be mentioned an alkyloxycarbonyl group of 2-6 carbon atoms such as ethoxycarbonyl, t-butoxycarbonyl and t-amyloxycarbonyl; a cycloalkyloxycarbonyl group of 4-7 carbon atoms such as cyclopentyloxycarbonyl and cyclohexyloxycarbonyl; an aralkyloxycarbonyl group such as benzyloxycarbonyl and p-nitrobenzyloxycarbonyl; an aryloxycarbonyl group such as phenoxycarbonyl; and furfuryloxycarbonyl and an acyl group such as o-nitrophenoxyacetyl and the like. When a pair of the groups $R_3$ and $R_4$ taken together forms a known di-valent amino-protecting group, this di-valent amino-protecting group may be a phthaloyl group or a salicylidene group, and generally an alkylidene or arylidene group of the formula =CHR$_5$ in which $R_5$ is an alkyl group of 1-6 carbon atoms such as methyl, ethyl, propyl, isopropyl, butyl or pentyl or an aryl group such as phenyl, tolyl, p-methoxyphenyl or o-hydroxyphenyl.

Such known mono-valent amino-protecting groups as alkyloxycarbonyl, aralkyloxycarbonyl or aryloxycarbonyl group may be shown by a formula —CO—OR$_6$ in which $R_6$ is an alkyl group of 1-5 carbon atoms such as methyl, ethyl, t-butyl and t-amyl or a cycloalkyl group of 3-6 carbon atoms such as cyclopentyl and cyclohexyl; an aralkyl group such as phenyl-alkyl group containing the alkyl of 1-4 carbon atoms, for example, benzyl and p-nitrobenzyl; an aryl group such as phenyl or a heterocyclic group such as furfuryl.

For the preparation of the amino-protected 6'N-methyl-3',4'-dideoxykanamycin B derivative (IV) of such type in which the 6'-methylamino group and the 2'-amino group have been blocked by a mono-valent amino-protecting group of the formula —CO—OR$_6$, 6'N-methyl-3',4'-dideoxykanamycin B (II) may be reacted with 2-3 molar proportions of a chloroformate of the formula

Cl—CO—OR$_6$     (VII);

or a p-nitrophenyl carbonate of the formula p-NO$_2$—C$_6$H$_5$—O—CO—OR$_6$     (VII');

or an N-hydroxysuccinimide ester of the formula

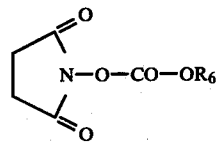

(VII");

or an azidoformate of the formula

N$_3$—CO—OR$_6$     (VII''');

or an S-4,6-dimethylpyrimid-2-ylthiocarbonate of the formula

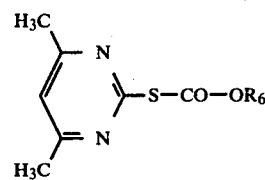

(VII'''');

wherein $R_6$ is as defined above, in a suitable solvent such as water, ethanol, acetone, dimethoxyethane or a mixture thereof under neutral or basic conditions in a manner known in the prior art for the synthesis of peptides. The reaction products so obtained usually consist of a mixture of various amino-protected derivatives of the compound (II), the main compound of which is an amino-protected derivative in which the 6'-methylamino group and the 2'-amino group have completely been blocked by the protective group —CO—OR$_6$, and a minor proportion of an amino-protected derivative in which only the 6'-methylamino group has been blocked, plus small amounts of undesired amino-protected derivatives in which the 1-amino group has been blocked together with the blocked amino groups. If the compound (II) is reacted with the acylating reagent (VII), (VII'), (VII") or (VII''') in substantially equimolar proportions, the proportion of the amino-protected derivative in which only the 6'-methylamino group has been blocked will be increased.

The most preferred amino-protecting groups are the t-butoxycarbonyl group and benzyloxycarbonyl group, as these are capable of reacting preferentially with the 6'-methylamino group and occasionally with the 2'-amino group of the 6'N-methyl-3',4'-dideoxykanamycin B compound (II), and then being readily removable from the acylated derivatives VI which are produced in the acylation step of the present process.

For instance, 2'N,6'N-di-t-butoxycarbonyl-6'N-methyl-3',4'-dideoxykanamycin B, a preferable starting material for the present process, may be prepared in a high yield by reacting 6'N-methyl-3',4'-dideoxykanamycin B in solution in a mixture of pyridine, water and triethylamine with a 2-3 molar proportion of t-butoxycarbonyl azide added dropwise thereto with agitation, stirring the resulting admixture at ambient temperature overnight, concentrating the reaction mixture to dryness in vacuo and then purifying the solid residue by column chromatography; or alternatively by reacting 6'N-methyl-3',4'-dideoxykanamycin B in the form of its aqueous solution with a 2-3 molar proportion of t-butyl S-4,6-dimethylpyrimid-2-ylthiocarbonate, which is added thereto under agitation, stirring the resulting admixture at ambient temperature overnight, concentrating the reaction mixture to dryness in vacuo and then purifying the solid residue by a column chromatography. The purification of said solid residue by column chromatography may be conducted using a cation-exchange resin having carboxylic functions, for example, a copolymer of methacyclic acid with divinylbenzene, e.g., a product known as "Amberlite" CG 50 (ammonium form; commercially available from Rohm & Haas, U.S.A.). The solid residue obtained in the above procedure comprises essentially the desired 2'N,6'N-di-t-butoxycarbonyl-6'N-methyl-3',4'-dideoxykanamycin and 6'N-mono-t-butoxycarbonyl-6'N-methyl-3',4'-dideoxykanamycin B and may directly be used as the raw material for the acylation step of the present process.

With respect to the α-hydroxy-ω-amino acid (V) which is employed as the acylating agent in the present process, the amino-protecting R₃ group may be those which are commonly used in the conventional synthesis of peptides. It is preferred that the amino-protecting group present in the acylating agent compound of the formula (V) be the same as that present in the starting amino-protected 6′N-methyl-3′,4′-dideoxykanamycin B derivative (IV). Preparation of the α-hydroxy-ω-amino acid reactant (V) of which the ω-amino group has been blocked by a mono-valent amino-protecting group may be carried out in the same manner as in the preparation of the amino-protected 6′N-methyl-3′,4′-dideoxykanamycin B derivative (IV). Where the groups R₃ and R₄ taken together form a di-valent amino-protecting group, this di-valent amino-protecting group may preferably be a phthaloyl or salicylidene group and may generally be an alkylidene or arylidene group of the formula =CHR₅ in which R₅ is an alkyl group of 1–6 carbon atoms such as methyl, ethyl, propyl, isopropyl, butyl or pentyl or an aryl group such as phenyl, tolyl, p-methoxyphenyl or o-hydroxyphenyl. Preparation of the α-hydroxy-ω-amino acid reactant (V) in which the ω-amino group has been blocked by a di-valent amino-protecting group of the formula =CHR₅ may be carried out by alkylidenating or arylidenating the ω-amino group by reacting the α-hydroxy-ω-amino acid reactant (V) with a substantially equimolar proportion of an aldehyde of the formula

  OHC—R₅ (VIII)

wherein R₅ is as defined above, in a manner known in the preparation of Schiff bases. Suitable aldehydes for this purpose include acetaldehyde, anisaldehyde, tolualdehyde, p-nitrobenzaldehyde and salicylaldehyde.

The α-hydroxy-ω-amino acid compound (V) employed in the present process may either be in the form of racemic mixture or in an optically active form; the L-isomer and the D-isomer. It is preferred, however, that α-hydroxy-γ-aminobutyric acid which is a compound of the formula (III) where n is 2, and α-hydroxy-δ-aminovaleric acid which is a compound of the formula (III) where n is 3 should be in the form of the optically active L-isomer, as the final product derived therefrom exhibits a higher antibacterial activity than the final product derived from the D-isomer.

In the acylation step of the process according to this invention, the amino-protected 6′N-methyl-3′,4′-dideoxykanamycin B derivative (IV) is reacted with the α-hydroxy-ω-amino acid reactant (V) in a manner known in the conventional preparation of amides. Thus, the starting compound (IV) may be reacted with the acylating reagent (V) in solution in anhydrous dimethylformamide, acetone or tetrahydrofuran under ice-cooling and in the presence of a dehydrating agent such as dicyclohexylcarbodiimide. Of course, the α-hydroxy-ω-amino acid reactant (V) may also be employed in the form of its functionally equivalent, reactive derivative such as the acid chloride, the mixed acid anhydride, the active esters or the azide derivative thereof. For instance, the α-hydroxy-ω-amino acid reactant (V) may first be reacted with N-hydroxysuccinimide in the presence of dicyclohexyl-carbodiimide as the dehydrating agent to prepare its active ester of the formula

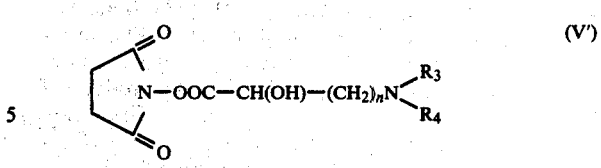

which is, in turn, reacted with the starting compound (IV) for the N-acylation of the latter compound. It is preferred that the starting compound (IV) should be reacted in a 0.5 to 3 molar proportion and preferably in a 0.5 to 1.5 molar proportion of the active ester form of the α-hydroxy-amino acid compound (V′) in a reaction medium consisting of water and an organic solvent such as dimethoxyethane.

In the acylating step of the present process, there is usually produced a mixture of mixed N-acylated derivatives of the starting compound (IV). The mixture generally consists of a mixture of the desired 1N-monoacylated derivative and other undesired mono-N-acylated derivatives and undesired poly-N-acylated derivatives. The mixture so produced may then directly be treated so as to remove any amino-protecting groups therefrom; that is to say, to convert the remaining amino-protecting groups into hydrogen atoms, respectively.

The removal of the amino-protecting groups from the above-mentioned mixed N-acylated derivatives which are produced by the acylation step of the present process may be effected in the following different ways known per se. Thus, when the amino-protecting group is an alkyloxycarbonyl group, such as t-butoxycarbonyl, an cycloalkyloxycarbonyl group, aryloxycarbonyl group, alkylidene or arylidene group, the removal of this kind of amino-protecting group may be effected by subjecting the mixed N-acylated derivatives to a mild hydrolysis treatment with an acid such as aqueous trifluoroacetic acid, aqueous acetic acid and diluted hydrochloric acid. When the amino-protecting groups is an aralkyloxycarbonyl group such as benzyloxycarbonyl, the removal of this type of amino-protecting group may be effected by subjecting the mixed N-acylated derivatives to a hydrogenolysis treatment in the presence of a palladium-carbon or platinum black catalyst or to a treatment with hydrogen bromide in acetic acid at low temperature. The o-nitrophenoxyacetyl amino-protecting group may be removed by a reductive treatment. When the amino-protecting group is phthaloyl group, the removal of the phthaloyl group may be achieved by treating the mixed N-acylated derivatives with hydrazine hydrate in ethanol. When the N-acylated derivatives contain different kinds of amino-protecting groups, the N-acylated derivatives may be subjected to simultaneous or successive treatments to remove the different amino-protecting groups therefrom.

The removal of the remaining amino-protecting groups gives a mixture of the differently N-acylated products derived from 6′N-methyl-3′,4′-dideoxykanamycin B. The mixture is comprised of the desired final product, 1N-(α-hydroxy-ω-aminoalkanoyl)-6′-N-methyl-3′,4′-dideoxykanamycin B, its position-isomers and the poly-N-acylated products, together with some unreacted 6′N-methyl-3′,4′-dideoxykanamycin B. The isolation of the desired final product of the formula (I) may efficiently be achieved by subjecting said mixture to column chromatography using, for example, silica gel or a cation-exchange resin having carboxylic functions, such as Amberlite IRC 50 or Amberlite CG 50 (a product of Rohm & Haas, Co., U.S.A.), a weak cation-exchanger such as CM-Sephadex C-25 (a product of Pharmacia Co., Sweden) or CM-cellulose. The eluate from the chromatographic process is collected in fractions, and the antibacterial activity of these fractions is detected using sensitive and resistant bacteria as the test microorganisms. Through the detection of the antibacterial activity of each fraction, it is relatively simple to determine the active fractions containing the desired compound of the formula (I). A portion of these active fractions were subjected to a thin layer chromatography with silica gel using, for example, a solvent system of butanol-ethanol-chloroform-17% aqueous ammonia. In this way, it was possible to determine the fractions which give a single spot at the specific Rf value of the desired 1 N-($\alpha$-hydroxy-$\omega$-aminoalkanoyl)-6' N-methyl-3',4'-dideoxykanamycin B of the formula (I) and hence it contains solely the desired product (I). Such fractions may be combined together and concentrated to dryness under reduced pressure to recover the desired compound (I).

The new compounds of the formula (I) according to this invention are useful to therapeutically treat bacterial infections as stated hereinbefore. According to a third aspect of this invention, therefore, there is provided a pharmaceutical composition for treating bacterial infections in living animals, including man, which comprises administering a therapeutically effective dose of a 1 N-($\alpha$-hydroxy-$\omega$-aminoalkanoyl)-6' N-methyl-3',4'-dideoxykanamycin B of the aforesaid formula (I); or a pharmaceutically acceptable acid-addition salt thereof as the active ingredient in combination with a pharmaceutically acceptable carrier for the active ingredient.

DESCRIPTION OF THE PREFERRED EMBODIMENTS

This invention is now illustrated with references to the following examples to which this invention is not limited in any way.

EXAMPLE 1

Synthesis of 1 N-(L-4-amino-2-hydroxybutyryl)-6' N-methyl-3',4'-dideoxykanamycin B (a compound of the formula (I) where n is 2).

(a) To a solution of 930 mg. (2 millimoles) of 6'N-methyl-3',4'-dideoxykanamycin B in 5 ml. of water was added a solution of 960 mg. (4 millimoles) of t-butyl S-4,6-dimethylpyrimid-2-ylthiocarbonate in 5 ml. of dioxane. The mixture was stirred overnight at ambient temperature to effect the t-butoxycarbonylation. The reaction mixture was then concentrated to dryness under reduced pressure to give a solid residue. This solid was taken up into 40 ml. of water and the insoluble matter was filtered off. The solution (the filtrate) was passed through a column (20 by 290 mm) of 100 ml. of a cation-exchange resin, Amberlite CO 50 (NH$_4$ form) to effect the adsorption of the t-butoxycarbonylation products by the resin. The resin column was washed with water (500 ml.) and then was eluted with 0.1N aqueous ammonia. Such fractions of the eluate which were positive to the ninhydrin reaction and to the Rydon-Smith reaction and which also gave a main spot at RF 0.60 by thin layer chromatography on silica gel using butanol-ethanol-chloroform-17% ammonia (4:5:2:3 by volume) as a developing solvent were combined together and concentrated to dryness under reduced pressure, affording 538 mg. of a colorless powder mainly comprising 2'N,6'N-di-t-butoxycarbonyl-6'N-methyl-3',4'-dideoxykanamycin B. Yield 41%.

(b) This colorless powder (100 mg.) mainly comprising 2'N,6'N-di-t-butoxycarbonyl-6'N-methyl-3',4'-dideoxykanamycin B (0.15 millimole) was dissolved in a mixture of 1 ml. of water and 1 ml. of dimethoxyethane, and to the resulting solution was added a solution of 54 mg. (0.17 millimole) of N-hydroxysuccinimide ester of L-4-t-butoxycarbonylamido-2-hydroxybutyric acid in 2 ml. of dimethoxymethane. The mixture was stirred for 22 hours at ambient temperature to effect the acylation of the amino-protected 6'N-methyl-3',4'-dideoxykanamycin B material. The reaction mixture was then concentrated to dryness under reduced pressure to afford a solid residue comprising the mixed N-acylated derivatives of the N-protected 6'N-methyl-3',4'-dideoxykanamycin B material.

(c) The solid residue from step b was dissolved in 2.4 ml. of aqueous 90% trifluoroacetic acid and the solution was allowed to stand for 1 hour at ambient temperature to effect the removal of the t-butoxycarbonyl group. The reaction mixture was concentrated to dryness under reduced pressure, and the residue was taken up into 4 ml. of water. The solution was adjusted to pH 8 by the addition of concentrated aqueous ammonia and then passed through a column (8 by 400 mm) of 20 ml. of a cation-exchange resin, Amberlite CG 50 (NH$_4$ form) to effect the adsorption of the mixed N-acylated 6'N-methyl-3',4'-dideoxykanamycin B products by the resin. After the resin column was washed successively with 100 ml. of water, with 100 ml. of 0.3 N aqueous ammonia and with 0.5 N aqueous ammonia, the resin column was eluted with 0.75 N aqueous ammonia. The eluate was collected in 2 ml. fractions, and every fraction was tested according to a usual plate method for their antibacterial activity against the kanamycin-sensitive strain *Bacillus subtilis* PCI 219 and kanamycin-resistant strain *Escherichia coli* JR66/W677. Those fractions which showed high antibacterial activity against both the above-mentioned strains were combined together (to a volume of 26 ml.) and then concentrated to dryness to give 39 mg. of a colorless powder mainly comprising the desired product, 1 N-(L-4-amino-2-hydroxybutyryl)-6'N-methyl-3',4'-dideoxykanamycin B. For further purification, this colorless powder was dissolved in 0.5 ml. of methanol-chloroform-17% aqueous ammonia (4:1:2 by volume), and the resulting solution was subjected to column chromatography on 3 g. of silica gel using methanol-chloroform-17% aqueous ammonia (4:1:2 by volume) as the eluant. The eluate was collected in 1 ml. fractions, and fraction Nos. 46–78 were found to contain solely 1 N-(L-4-amino-2-hydroxybutyryl)-6'N-methyl-3',4'-dideoxykanamycin B which gave a single spot of Rf 0.38 in a thin layer chromatography on silica gel ("ART" 5721) using butanol-ethanol-chloroform-28% aqueous ammonia (4:5:2:8 by volume) as eluant. These fractions were combined together and concentrated to dryness to give 15 mg. of pure 1 N-(L-4-amino-2-hydroxybutyryl)-6'N-methyl-3',4'-dideoxykanamycin B as a colorless powder. Decomposition point; 158°–161° C.

EXAMPLE 2

Synthesis of 1 N-(DL-isoseryl)-6'N-methyl-3',4'-dideoxykanamycin B (a compound of the formula (I) where n is 1).

(a) The colorless powder (403 mg.) mainly comprising 2'N,6'N-di-t-butoxycarbonyl-6'N-methyl-3',4'-dideoxykanamycin B (0.6 millimole) which was obtained in Example 1(a) was dissolved in a mixture of 4 ml. of water and 4 ml. of dimethoxyethane. The solution so obtained was admixed with a solution of 221 mg. (0.66 millimole) of N-hydroxysuccinimide ester of N-t-butoxycarbonyl-DL-isoserine in 8 ml. of dimethoxyethane. The admixture was stirred for 23.5 hours at ambient temperature to effect the acylation. The reaction mixture was then concentrated to dryness under reduced pressure to give a solid residue mainly comprising the mixed N-acylated derivatives of 2'N,6'N-di-t-butoxycarbonyl-6'N-methyl-3',4'-dideoxykanamycin B.

(b) This solid residue product was dissolved in 7.5 ml. of aqueous 90% trifluoroacetic acid, and the solution was allowed to stand for 1 hour at ambient temperature to effect the removal of the t-butoxycarbonyl group. The reaction mixture was concentrated to dryness under reduced pressure, and the residue was dissolved in 16 ml. of water. The aqueous solution so obtained was adjusted to pH 8 by addition of concentrated aqueous ammonia and was then passed through a column (10 by 560 mm) of 43 ml. of a cation-exchange resin, Amberlite CG 50 ($NH_4$ form) to effect the adsorption of the mixed N-acylated products. The resin column was washed with 200 ml. of water and then with 400 ml. of 0.3N aqueous ammonia and was subsequently eluted with 0.5 N aqueous ammonia. The eluate was collected in 4 ml. fractions, and every fraction was tested according to a usual plate method for their antibacterial activity against *Bacillus subtilis* PCI 219 and *Escherichia coli* JR66/W677. The fractions which showed a high antibacterial activity against these two strains were combined together (to a volume of 100 ml.) and then concentrated to dryness to give 135 mg. of a colorless powder mainly comprising the desired product, 1 N-(DL-isoseryl)-6'N-methyl-3',4'-dideoxykanamycin B. Fur further purification, this colorless powder was dissolved in 2.6 ml. of methanol-chloroform-17% aqueous ammonia (4:1:2 by volume), and the resulting solution was subjected to a column chromatography on silica gel (8 g.) using methanol-chloroform-17% aqueous ammonia (4:1:2 by volume) as eluant. The eluant was collected in 2 ml. fractions, and fraction Nos. 20–27 were found to contain solely the desired product which gave a single spot of 0.51 in a thin layer chromatography on silica gel ("ART" 5721) using butanol-ethanol-chloroform-28% aqueous ammonia (4:5:2:8 by volume) as eluant. These fractions were combined together and concentrated to dryness to give 38 mg. of pure 1N-(DL-isoseryl)-6'N-methyl-3',4'-dideoxykanamycin B as a colorless powder. Decomposition point; 165°–169° C.

EXAMPLE 3

Synthesis of 1N-(L-isoseryl)-6'N-methyl-3',4'-dideoxykanamycin B (a compound of the formula (I) where n is 1).

(a) t-Butoxycarbonyl azide (465 mg.; 3.2 millimoles) was added to a solution of 500 mg. (1.1 millimoles) of 6'N-methyl-3',4'-dideoxykanamycin B in a mixture of 21 ml. of pyridine, 21 ml. of triethylamine and 12.6 ml. of water. The mixture was stirred overnight at ambient temperature to effect the t-butoxycarbonylation. The reaction mixture was concentrated to dryness under reduced pressure, to afford 727 mg. of a colorless powder mainly comprising a mixture of 2'N,6'N-di-t-butoxycarbonyl-6'N-methyl-3',4'-dideoxykanamycin B and 6'N-t-butoxycarbonyl-6'N-methyl-3',4'-dideoxykanamycin B.

(b) The above colorless powder (510 mg.) mainly comprising a mixture of the partly amino-protected derivatives of 6'N-methyl-3',4'-dideoxykanamycin B was, without purification thereof, dissolved in a mixture of 5 ml. of water and 5 ml. of dimethoxyethane. To the resulting solution was added a solution of 254 mg. (0.84 millimole) of N-hydroxysuccinimide ester of N-t-butoxycarbonyl-L-isoserine in 10 ml. of dimethoxyethane. The mixture was stirred for 19 hours at ambient temperature to effect the acylation. The reaction mixture was concentrated to dryness under reduced pressure to give 794 mg. of a solid residue comprising the mixed N-acylated derivatives of 2'N,6'N-di-t-butoxycarbonyl- and 6'N-t-butoxycarbonyl-6'N-methyl-3',4'-dideoxykanamycin B.

(c) The solid residue product was treated with aqueous 90% trifluoroacetic acid for the removal of the t-butoxycarbonyl group, and was then subjected to the purification by column chromatography with Amberlite CG 50 and subsequently to purification by column chromatography on silica gel in the same manner as in Example 2(b). Pure 1N-(L-isoseryl)-6'N-methyl-3',4'-dideoxykanamycin B was obtained as a colorless powder. Yield 34 mg. Decomposition point; 162°–166° C.

EXAMPLE 4

Synthesis of 1N-(L-5-amino-2-hydroxyvaleryl)-6'N-methyl-3',4'-dideoxykanamycin B (a compound of the formula (I) where n is 3).

(a) The colorless powder (510 mg.) mainly comprising a mixture of 2'N,6'N-di-t-butoxycarbonyl-6'N-methyl-3',4'-dideoxykanamycin B and 6'N-t-butoxycarbonyl-6'N-methyl-3',4'-dideoxykanamycin B which was prepared in the same manner as in Example 3(a) was, without purification thereof, dissolved in a mixture of 5 ml. of water and 5 ml. of dimethoxyethane. To the resulting solution was added a solution of 278 mg. (0.84 millimole) of N-hydroxysuccinimide ester of L-5-t-butoxycarbonylamido-2-hydroxyvaleric acid in 10 ml. of dimethoxyethane. The mixture was stirred for 18 hours at ambient temperature to effect the acylation. The reaction mixture was concentrated to dryness under reduced pressure to give 834 mg. of the solid residue comprising the mixed N-acylated derivatives of the 2'N,6'N-di-t-butoxycarbonyl- and 6'N-t-butoxycarbonyl-6'N-methyl-3',4'-dideoxykanamycins B.

(b) The solid residue product was dissolved in 8 ml. of aqueous 90% trifluoroacetic acid, and the solution was allowed to stand for 1 hour at ambient temperature to effect the removal of the t-butoxycarbonyl group. The reaction mixture was concentrated to dryness under reduced pressure, and the residue so obtained was taken up into 16 ml. of water. The resultant aqueous solution was adjusted to pH 8.4 by addition of concentrated, aqueous ammonia and was then adsorbed on column (10 by 560 mm) of 40 ml. of Amberlite CG-50 resin ($NH_4$ form). After the resin column was washed successively with 200 ml. of water, with 250 ml. of 0.3 N aqueous ammonia and with 240 ml. of 0.5 N aqueous ammonia, the resin column was eluted with 0.75 N aqueous ammonia. The eluate was collected in 4 ml. fractions, and such fractions which showed a high antibacterial activity against *Bacillus subtilis* PCI 219 and *Escherichia coli* JR66/W677 were detected, combined together (to a volume of 60 ml.), concentrated to dryness and then chromatographed in a silica gel column in the same manner as in Example 1(c). Pure 1N-(L-5-amino-2-hydroxylvaleryl)-6′N-methyl-3′,4′-dideoxykanamycin B was obtained as a colorless powder. Yield 29 mg. Decomposition point; 152°–155° C.

We claim:

1. A 1N-(α-hydroxy-ω-aminoalkanoyl)-6′N-methyl-3′,4′-dideoxykanamycin B of the formula:

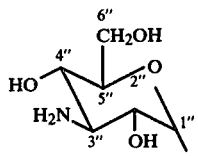
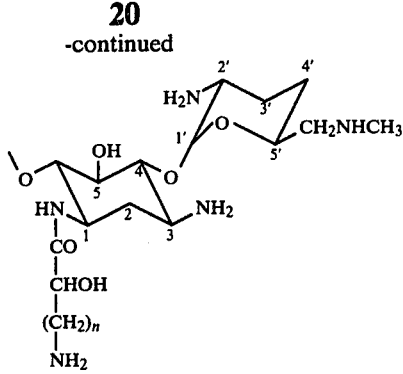

wherein n is 1, 2 or 3; or a pharmaceutically acceptable acid addition salt thereof.

2. A compound of claim 1 which is 1N-(DL-isoseryl)-6′N-methyl-3′,4′-didexoykanamycin B; or a pharmaceutically acceptable acid addition salt thereof.

3. A compound of claim 1 which is 1N-(L-isoseryl)-6′N-methyl-3′,4′-dideoxykanamycin B; or a pharmaceutically acceptable acid addition salt thereof.

4. A compound of claim 1 which is 1N-(L-4-amino-2-hydroxybutyryl)-6′N-methyl-3′,4′-dideoxykanamycin B; or a pharmaceutically acceptable acid addition salt thereof.

5. A compound of claim 1 which is 1N-(L-5-amino-2-hydroxyvaleryl)-6′N-methyl-3′,4′-dideoxykanamycin B; or a pharmaceutically acceptable acid addition salt thereof.

* * * * *